(12) United States Patent
Yousef et al.

(10) Patent No.: US 12,257,239 B1
(45) Date of Patent: *Mar. 25, 2025

(54) CYTOTOXIC TREATMENT OF CANCER CELLS

(71) Applicant: IMAM MOHAMMAD IBN SAUD ISLAMIC UNIVERSITY, Riyadh (SA)

(72) Inventors: Tarek Ahmed Yousef, Riyadh (SA); Saad Shaaban, Almansourah (EG); Ahmed A. Al-Karmalawy, Riyadh (SA); Marwa Sharaky, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/939,592

(22) Filed: Nov. 7, 2024

Related U.S. Application Data

(63) Continuation of application No. 18/799,676, filed on Aug. 9, 2024, now Pat. No. 12,178,806, which is a continuation of application No. 18/661,337, filed on May 10, 2024, now Pat. No. 12,115,148.

(51) Int. Cl.
*A61K 31/427* (2006.01)

(52) U.S. Cl.
CPC ................... *A61K 31/427* (2013.01)

(58) Field of Classification Search
CPC .................................................... A61K 31/427
See application file for complete search history.

(56) References Cited

U.S. PATENT DOCUMENTS

| | | | |
|---|---|---|---|
| 5,478,850 A | 12/1995 | Hindley et al. | |
| 7,153,875 B2 | 12/2006 | Pfahl et al. | |
| 7,226,940 B2 | 6/2007 | Pfahl et al. | |
| 7,973,062 B2 | 7/2011 | Chen et al. | |

FOREIGN PATENT DOCUMENTS

CN 103099809 A 5/2013

OTHER PUBLICATIONS

Muhammad Shah, et al., "SAR and lead optimization of (Z)-5-(4-hydroxy-3-methoxybenzylidene)-3-(2-morpholinoacetyl)thiazolidine-2,4-dione as a potential multi-target antidiabetic agent", European Journal of Medicinal Chemistry, vol. 258, Oct. 5, 2023, p. 115591.

*Primary Examiner* — Kamal A Saeed
(74) *Attorney, Agent, or Firm* — Oblon, McClelland, Maier & Neustadt, L.L.P.

(57) ABSTRACT

A method for cytotoxically treating cancer cells includes contacting the cancer cells with a composition comprising a compound of Formula I. The compound of Formula I is contacted with the cancer cells in an amount effective to reduce the number of cancer cells by at least 50%. A method for preparing the compound of Formula I.

20 Claims, 2 Drawing Sheets

Formula I

CYTOTOXIC TREATMENT OF CANCER CELLS

CROSS-REFERENCE TO RELATED APPLICATIONS

The present application is a Continuation of U.S. application Ser. No. 18/799,676, now allowed, having a filing date of Aug. 9, 2024, which is a Continuation of U.S. application Ser. No. 18/661,337, now U.S. Pat. No. 12,115,148, having a filing date of May 10, 2024.

BACKGROUND

Technical Field

The present disclosure relates to the treatment of cancer cells, and particularly to a method for contacting cancer cells with a cytotoxically effective amount of a thiazolidine dione compound.

Description of Related Art

The "background" description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Cancer is a dangerous illness that is defined by aberrant cells growing and spreading out of control. It is a global health problem responsible for one in six deaths worldwide. In 2020 there were an estimated 19.3 million new cancer cases and about 10 million cancer deaths globally. Genetic alterations that disrupt cells' regular cycles of growth, division, and death are the first step toward the development of cancer. Lung cancer, breast cancer, prostate cancer, colorectal cancer, leukemia, and the like are common cancer types. Apoptosis, also known as programmed cell death or cellular suicide, is a biological mechanism that eliminates harmful, old, and/or unimportant cells, limiting the growth of aberrant cells, like cancer cells. DNA damage, oxidative stress, and nutritional deprivation are examples of intrinsic processes that control apoptosis. Extrinsic pathways include activating death receptors on the cell surface and the like. The Bcl-2 family and caspases are contributing components of the apoptotic process. Caspases are regarded as protease enzymes that contribute to the start and completion of apoptosis. They cause the cell to break down by cleaving particular biological proteins. The Bcl-2 family modifies the permeability of the mitochondrial membrane to regulate the intrinsic route. While some members of the Bcl-2 family are anti-apoptotic, others are pro-apoptotic. With the growing understanding of apoptosis, cancer medicines that cause malignant cells to undergo apoptosis have been developed. Therefore, one target for therapeutic treatments in cancer treatment is regulating apoptosis.

There have been few options for cancer treatment for patients for many decades, which include surgery, radiation therapy, and chemotherapy as single treatments or in combination. Recently, many pathways involved in cancer therapy progression and how they can be targeted, such as combinatorial strategies involving multiple targeted therapies, "traditional" chemotherapeutics, and/or the like, have improved [Debela et al., New approaches and procedures for cancer treatment: Current perspectives, *SAGE Open Medicine* 9 (2021) 1-10]. With growing health concerns of cancer across the globe, continuous research efforts in this domain would pave the way for effectively combating this disease.

Accordingly, an object of the present disclosure is to provide a method of cytotoxically treating cancer cells to overcome shortcomings of known cancer cell treatments.

SUMMARY

In an exemplary embodiment, a method of cytotoxically treating cancer cells is described. The method includes contacting the cancer cells with a composition comprising a compound of Formula I:

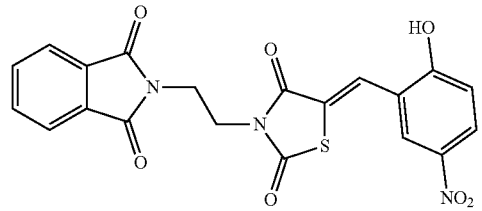

Formula I wherein the compound of formula I is contacted with the cancer cells in an amount effective to reduce the number of cancer cells by at least 50%.

In some embodiments, the method includes contacting the cancer cells with the composition for inhibiting cell growth of the cancer cells through apoptosis.

In some embodiments, the apoptosis occurs through at least one of a p53 pathway, a BAX pathway, a caspases pathway, a BCL-2 pathway, an MMP2 pathway, and an MMP9 pathway.

In an exemplary embodiment, a method of making the compound of Formula I is described. The method includes dissolving 3-(2-(1,3-dioxoisoindolin-2-yl)ethyl)thiazolidine-2,4-dione and 2-hydroxy-5-nitrobenzaldehyde in a polar protic solvent to form a reaction mixture; adding an acid and a heterocyclic amine to the reaction mixture; and refluxing the reaction for 6 to 10 hours to form the compound of Formula I.

In some embodiments, wherein a molar ratio of 3-(2-(1,3-dioxoisoindolin-2-yl)ethyl)thiazolidine-2,4-dione to 2-hydroxy-5-nitrobenzaldehyde is from 1:0.8 to 1:1.5.

In some embodiments, the compound of Formula I is formed in a yield of 83 to 87% based on an initial amount of the 3-(2-(1,3-dioxoisoindolin-2-yl)ethyl)thiazolidine-2,4-dione.

In some embodiments, the method includes contacting the cancer cells with the composition by contacting the compound of Formula I with human non-small cell lung cancer cells, A549, at a concentration of 100 µg/mL to provide a growth inhibition percentage of 76 to 80%.

In some embodiments, the method includes contacting the cancer cells with the composition by contacting the compound of Formula I with colorectal carcinoma cells, HCT116, at a concentration of 100 µg/mL to provide a growth inhibition percentage of 84 to 88%.

In some embodiments, the method includes contacting the cancer cells with the composition by contacting the compound of Formula I with prostate cancer cells, PC3, at a concentration of 100 µg/mL to provide a growth inhibition percentage of 82 to 86%.

In some embodiments, the method includes contacting the cancer cells with the composition by contacting the compound of Formula I with pharynx squamous carcinoma cells, FaDu, at a concentration of 100 μg/mL to provide a growth inhibition percentage of 87 to 92%.

In some embodiments, the method includes contacting the cancer cells with the composition by contacting the compound of Formula I with triple-negative breast cancer cells, MDA-MB-468, at a concentration of 100 μg/mL to provide a growth inhibition percentage of 89 to 94%.

In some embodiments, the method includes contacting the cancer cells with the composition by contacting the compound of Formula I with cervical cancer cells, HeLa, at a concentration of 100 μg/mL to provide a growth inhibition percentage of 69 to 73%.

In some embodiments, the method of contacting the cancer cells includes contacting the compound of Formula I with human non-small cell lung cancer cells, A549, to provide a half-maximal inhibitory concentration ($IC_{50}$) value of 5.5 to 6.5 μg/mL.

In some embodiments, the method of contacting the cancer cells includes contacting the compound of Formula I with pharynx squamous carcinoma cells, FaDu, to provide an $IC_{50}$ value of 4.5 to 5.5 μg/mL.

In some embodiments, the method of contacting the cancer cells includes contacting the compound of Formula I with triple-negative breast cancer cells, MDA-MB-468, to provide an $IC_{50}$ value of 5 to 6 μg/mL for a.

In some embodiments, the method of contacting the cancer cells includes contacting the compound of Formula I with cervical cancer cells, HeLa, to provide an $IC_{50}$ value of 4.5 to 5.5 μg/mL.

In some embodiments, the method of contacting the cancer cells includes contacting the compound of Formula I with human oral epithelial normal cells, OEC, at a concentration of 100 μg/mL to provide a growth inhibition percentage of 47 to 51%.

In some embodiments, the composition further comprises one or more pharmaceutically acceptable carriers.

In some embodiments, the composition is in the form of a pill, a liquid, a shot, a cream, and a patch.

In some embodiments, the compound of Formula I has a melting point of 252 to 259° C.

These and other aspects of the non-limiting embodiments of the present disclosure will become apparent to those skilled in the art upon review of the following description of specific non-limiting embodiments of the disclosure in conjunction with the accompanying drawings. The foregoing general description of the illustrative present disclosure and the following detailed descriptions thereof are merely exemplary aspects of the teachings of this disclosure and are not restrictive.

BRIEF DESCRIPTION OF THE DRAWINGS

A more complete appreciation of this disclosure (including alternative and/or variations thereof) and many of the attendant advantages thereof will be readily obtained as the same becomes better understood by reference to the following detailed description when considered in connection with the accompanying drawings, wherein.

DETAILED DESCRIPTION

Figure 1:
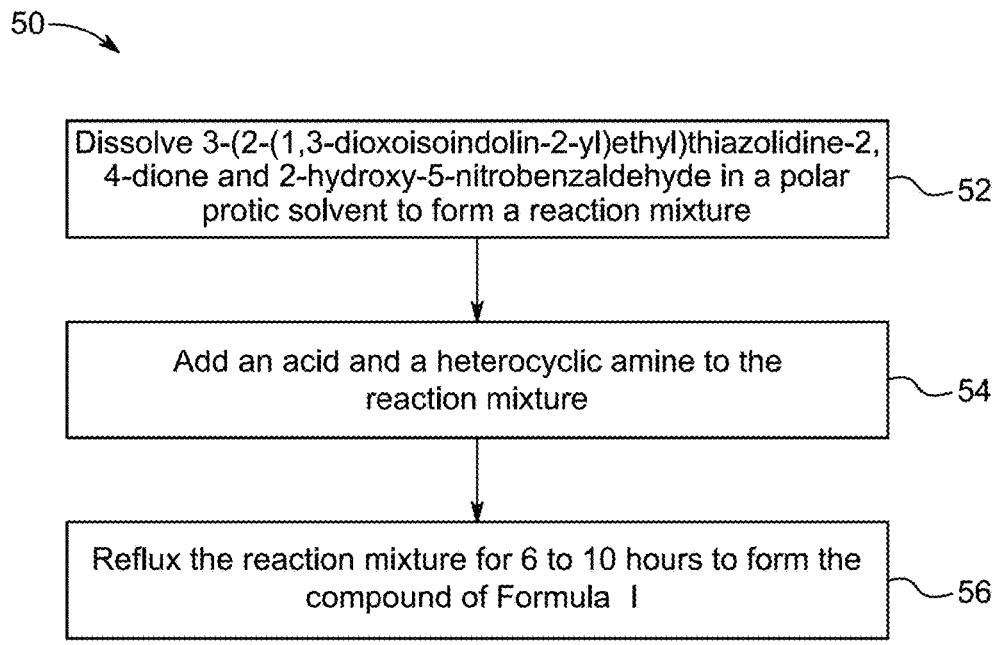
FIG. 1 is a flow chart depicting a method of forming a compound of Formula I, according to some embodiments.

In the following description, it is understood that other embodiments may be utilized, and structural and operational changes may be made without departure from the scope of the present embodiments disclosed herein.

Reference will now be made to specific embodiments or features, examples of which are illustrated in the accompanying drawings. In the drawings, whenever possible, corresponding or similar reference numerals will be used to designate identical or corresponding parts throughout the several views. Moreover, references to various elements described herein are made collectively or individually when there may be more than one element of the same type. However, such references are merely exemplary in nature. It may be noted that any reference to elements in the singular may also be constructed to relate to the plural and vice-versa without limiting the scope of the disclosure to the exact number or type of such elements unless set forth explicitly in the appended claims. Further, as used herein, the words "a," "an," and the like generally mean "one or more," unless stated otherwise.

Furthermore, the terms "approximately," "approximate," "about," and similar terms generally refer to ranges that include the identified value within a margin of 20%, 10%, or preferably 5%, and any values therebetween.

As used herein, the term "cancer" refers to any one of a large number of diseases characterized by the development of abnormal cells that divide uncontrollably and have the ability to infiltrate and destroy normal body tissue, and may refer to all types of cancer, neoplasm, and/or malignant tumors found in mammals (e.g., humans), including leukemias, lymphomas, carcinomas, sarcomas, and the like. Exemplary cancers that may be treated with the method or composition provided herein include brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with the method provided herein include cancer of the thyroid, endocrine system, brain, breast, cervix, colon, head and neck, liver, kidney, lung, ovary, pancreas, rectum, stomach, and uterus. Additional examples include, but are not limited to, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulinoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, prostate cancer, and the like.

As used herein, the term "half maximal inhibitory concentration ($IC_{50}$)" refers to the measure of the potency of a substance in inhibiting a specific biological or biochemical function. $IC_{50}$ is a quantitative measure that indicates how much of a particular inhibitory substance (e.g., drug) is needed to inhibit, in vitro, a given biological process or biological component by 50%. The biological component can be an enzyme, cell, cell receptor, microorganism, and the like. $IC_{50}$ values are typically expressed as molar concentration.

As used herein, "analogue" and "analog" refer to a chemical compound that is structurally similar to a parent compound, but differs slightly in composition (e.g., one atom or functional group is different, added, and/or removed). The analogue may or may not have different chemical or physical properties than the original compound and may or may not have improved biological and/or chemical activity. For example, the analogue may be more hydrophilic, or it may have altered reactivity as compared to the parent compound. The analogue may mimic the chemical and/or biologically active of the parent compound (i.e., it may have similar or identical activity), or, in some cases, may have increased or decreased activity. The analogue may be a naturally or non-naturally occurring variant of the original compound. Other types of analogues include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not be used as the starting material to generate an "analogue." A derivative may or may not have different chemical or physical properties of the parent compound. For example, the derivative may be more hydrophilic, or it may have altered reactivity as compared to the parent compound. Derivatization (i.e., modification) may involve the substitution of one or more moieties within the molecule (e.g., a change in a functional group). The term "derivative" also includes conjugates, and prodrugs of a parent compound (i.e., chemically modified derivatives that can be converted into the original compound under physiological conditions). A "prodrug" is meant to indicate a compound that can be converted under physiological conditions or by solvolysis to a biologically active compound. Thus, the term "prodrug" refers to a precursor of a biologically active compound that is pharmaceutically acceptable. A prodrug may be inactive when administered to a subject, but is converted in vivo to an active compound, for example, by hydrolysis.

The terms "cytotoxically effective amount" and "therapeutically effective amount" as used herein refer to the amount of the complex being administered which will relieve, to some extent, one or more of the symptoms of the disorder being treated. A cytotoxically effective amount and therapeutically effective amount may be at a level that will exercise the desired effect. In reference to cancer or pathologies related to increased cell division, a cytotoxically effective amount and therapeutically effective amount refer to an amount which has the effect of at least one of the following: (1) reducing the size of a tumor; (2) inhibiting (that is, slowing to some extent, preferably stopping) aberrant cell division, growth, and/or proliferation, for example, cancer cell division; (3) preventing or reducing the metastasis of cancer cells; (4) relieving to some extent (or, preferably, eliminating) one or more symptoms associated with a pathology related to or caused in part by unregulated or aberrant cellular division, including for example, cancer; and (5) inducing apoptosis of cancer cells or tumor cells.

As used herein, the terms "therapies" and "therapy" may refer to any method(s), composition(s), and/or agent(s), and/or complex(es) that can be used in the prevention, treatment, and/or management of a cancer, disease, or one or more symptoms thereof. Therapy may include immunotherapy, radiation therapy, drug therapy, chemotherapy, combination therapy, and the like.

As used herein, the terms "treat," "treatment," and "treating" in the context of the administration of a therapy to a subject in need thereof refer to the reduction or inhibition of the progression and/or duration of cancer, the reduction or amelioration of the severity of cancer, and/or the amelioration of one or more symptoms thereof resulting from the administration of one or more therapies. In some embodiments, the subject is a mammalian subject. In one embodiment, the subject is a human. "Treating" or "treatment" of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). "Treat," "treating," "treatment," and the like, as used herein, refer to any action providing a benefit to a subject at risk for or afflicted with a condition or disease such as cancer, including improvement in the condition through lessening or suppression of at least one symptom, delay in progression of the disease, prevention or delay in the onset of the disease, and the like. The subject may be at risk due to exposure to carcinogenic agents, being genetically predisposed to disorders, and so on. With regard to cancer or hyperplasia, these terms simply mean that the life expectancy of an individual affected with cancer will be increased or that one or more of the symptoms of the disease will be reduced. In specific embodiments, such terms refer to one, two, three, or more results following the administration of one, two, three, or more therapies: (1) a stabilization, reduction, or elimination of the cancer stem cell population; (2) a stabilization, reduction, or elimination in the cancer cell population; (3) a stabilization or reduction in the growth of a tumor or neoplasm; (4) an impairment in the formation of a tumor; (5) eradication, removal, or control of primary, regional, and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; and (12) an increase in the number of patients in remission. In certain embodiments, such terms refer to a stabilization or reduction in cancer stem cell population. In some embodiments, such terms refer to a stabilization or reduction in the growth of cancer cells. In some embodiments, such terms refer to stabilization or reduction in cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in the survival rate of a patient population. In further embodiments, such terms refer to an increase in the response rate, the durability of response, or the number of patients who respond or are in remission. In some embodiments, such terms refer to a decrease in the hospitalization rate of a patient population and/or a decrease in hospitalization length for a patient population.

As used herein, a "pharmaceutical composition" refers to a mixture of the compounds described herein or pharmaceutically acceptable salts, esters, or prodrugs thereof, with other chemical components, such as physiologically acceptable carriers and excipients. A pharmaceutical composition may be formulated to contain a daily dose, or convenient fraction of a daily dose, in a dosage unit. In general, the pharmaceutical composition is prepared according to methods in pharmaceutical chemistry.

"Pharmaceutically acceptable," as used herein, means that the compound or composition is suitable for administration to a subject for the methods described herein, without unduly deleterious side effects in light of the severity of the disease and necessity of the treatment.

The terms "cytotoxically effective," "therapeutically effective," and "pharmacologically effective" are intended to qualify the amount of each agent which will achieve the goal of decreasing disease severity while avoiding adverse side effects, such as those typically associated with alternative therapies. The cytotoxically effective amount and the therapeutically effective amount may be administered in one or more doses. An effective amount, on the other hand, is an amount sufficient to provide a chemical effect.

"Pharmaceutically acceptable salt" or "pharmaceutically acceptable ester" refers to a compound in a pharmaceutically acceptable form, (such as an ester, a phosphate ester, a salt of an ester, or a related) which, upon administration to a subject in need thereof, provides the compound of Formula I described herein. Pharmaceutically acceptable salts and esters retain the biological effectiveness and properties of the free bases, which are obtained by reaction with inorganic or organic acids, such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Suitable salts include those derived from alkali metals such as potassium and sodium, and alkaline earth metals such as calcium and magnesium, among numerous other acids well-known in the art.

As used herein, a "pharmaceutically acceptable carrier" refers to a carrier or vehicle which may comprise an excipient, diluent, or mixture thereof that does not cause irritation to an organism and does not abrogate the biological activity and properties of the compound of Formula I. The term carrier encompasses any excipient, diluent, filler, salt, buffer, stabilizer, solubilizer, lipid, stabilizer, or other material well known in the art for use in pharmaceutical formulations. Suitable formulations may be prepared by methods commonly employed using conventional, organic, and inorganic additives, such as an excipient selected from fillers or diluents, binders, disintegrants, lubricants, flavoring agents, preservatives, stabilizers, suspending agents, dispersing agents, surfactants, antioxidants, solubilizers, and the like. The choice of a carrier for use in a composition may depend upon the intended route of administration for the composition. The preparation of pharmaceutically acceptable carriers and formulations containing these materials is described in, for example, Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffers, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

An "excipient" refers to an inert substance added to a pharmaceutical composition to facilitate the administration of a compound further. Examples, without limitation, of excipients include fillers or diluents (e.g., sucrose, starch, mannitol, lactose, glucose, cellulose, talc, calcium carbonate, calcium phosphate, and the like), a binder (e.g., cellulose, carboxymethylcellulose, methylcellulose, hydroxy methylcellulose, hydroxypropyl methylcellulose, polypropylpyrrolidone, polyvinylpyrrolidone, gelatin, gum Arabic, polyethylene glycol, starch, and the like), a disintegrant (e.g., sodium starch glycolate, croscarmellose sodium, and the like), a lubricant (e.g., magnesium stearate, light anhydrous silicic acid, talc, sodium lauryl sulfate, and the like), a flavoring agent (e.g., citric acid, methanol, and the like), a preservative (e.g., sodium benzoate, sodium bisulfate, methylparaben, propylparaben, and the like), a stabilizer (e.g., citric acid, sodium citrate, acetic acid, and the like), a dispersing agent (e.g., hydroxypropyl methylcellulose and the like), antioxidants (e.g., ethylene diamine tetraacetic acid (EDTA), butylated hydroxyl toluene (BHT), and the like), solubilizers (e.g., polyethylene glycols and the like), various sugars and types of starch, cellulose derivatives, gelatin, vegetable oils, and polyethylene glycols.

Unless otherwise noted, the present disclosure is intended to include all isotopes of the samples used herein.

Aspects of this disclosure are directed to cytotoxic compounds of Formula I and methods of contacting cancer cells with the cytotoxic compounds in a cytotoxically effective amount. The compound was synthesized and evaluated for antitumor activity in various cancer cell lines. The antiproliferative effect (e.g., cytotoxic effect) of Formula I was found to be comparable to doxorubicin (DOX) in non-small cell lung cancer (A549), colorectal carcinoma (HCT116), prostate cancer (PC3), pharynx squamous carcinoma (FaDu), triple-negative breast cancer (MDA-MB-468), and cervical cancer (HeLa) cell lines and greater in colorectal carcinoma (HCT116).

Aspects of the present disclosure are directed to a method of cytotoxically treating cancer cells. The method includes contacting the cancer cells with a composition including a compound of Formula I described herein, or analogues or derivatives thereof:

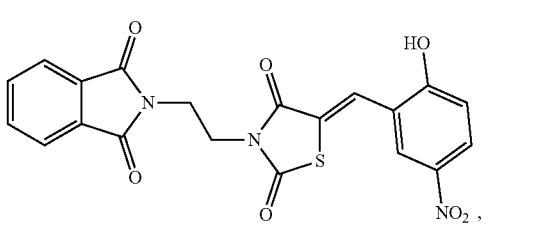 [SMILES: O=C1S/C(=C\c2cc([N+](=O)[O-])ccc2O)C(=O)N1CCN1C(=O)c2ccccc2C1=O]

Formula I wherein the compound of Formula I is contacted with the cancer cells in an amount effective to reduce the number of cancer cells by at least 50%, preferably at least 55%, preferably at least 60%, preferably at least 65%, preferably at least 70%, preferably at least 75%, preferably at least 80%, more preferably at least 85%, and yet more preferably at least 90%.

Contacting the cancer cells with the compound Formula I initiates apoptosis, resulting in the inhibition of cell growth. The apoptosis occurs through at least one of a p53 pathway, a BAX pathway, a caspases pathway, a BCL-2 pathway, an MMP2 pathway, and an MMP9 pathway.

Referring to FIG. 1, a method 50 of making the compound of Formula I is described. The order in which the method 50 is described is not intended to be construed as a limitation, and any number of the described method 50 steps may be combined in any order to implement the method 50. Additionally, individual steps may be removed or skipped from method 50 without departing from the spirit and scope of the present disclosure.

At step 52, the method 50 includes dissolving 3-(2-(1,3-dioxoisoindolin-2-yl)ethyl)thiazolidine-2,4-dione and 2-hydroxy-5-nitrobenzaldehyde in a polar protic solvent to form a reaction mixture. The molar ratio of 3-(2-(1,3-dioxoisoindolin-2-yl)ethyl)thiazolidine-2,4-dione to 2-hydroxy-5-nitrobenzaldehyde is from 1:0.8 to 1:1.5, preferably 1:0.9 to 1:1.4, preferably 1:1 to 1:1.3, more preferably 1:1.05 to 1:1.2, and yet more preferably about 1:1.1. Both these compounds are dissolved in a polar protic solvent. Suitable examples of the polar protic solvent include, but are not limited to, water, ethanol, methanol, isopropanol, ammonia, formic acid, acetic acid, and the like. In a preferred embodiment, the polar protic solvent is ethanol.

At step 54, the method 50 includes adding an acid and a heterocyclic amine to the reaction mixture. Suitable examples of the acid include, formic acid, acetic acid, oxalic acid, benzoic acid, and the like. In a preferred embodiment, the acid is acetic acid. The heterocyclic amine includes at least one heterocyclyl group and at least one amine. The heterocyclyl group may be oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl azepanyl, and the like, which may be optionally substituted. In a preferred embodiment, the heterocyclic amine is piperidine. The volume ratio of the acid to the heterocyclic amine is in the range of 1:5 to 5:1, preferably 1:4 to 4:1, preferably 1:3 to 3:1, preferably 1:2 to 2:1, and yet more preferably about 1:1.

At step 56, the method 50 includes refluxing the reaction mixture for 6 to 10 hours, preferably 7 to 9 hours, and more preferably about 8 hours, to form the compound of Formula I. In some embodiments, the compound of Formula I is formed in a yield of 83 to 87%, preferably 84 to 86%, and more preferably about 85%, based on an initial amount of the 3-(2-(1,3-dioxoisoindolin-2-yl)ethyl)thiazolidine-2,4-dione. The compound of Formula I has a melting point of 252 to 259° C., preferably 253 to 258° C., more preferably 254 to 257° C., and yet more preferably about 255 to 256° C.

The compound of Formula I was tested for its antitumor activity against various cancer cell lines, in vitro, in non-small cell lung cancer (A549), colorectal carcinoma (HCT116), prostate cancer (PC3), pharynx squamous carcinoma (FaDu), triple-negative breast cancer (MDA-MB-468), cervical cancer (HeLa), and human oral epithelial normal cell line (OEC).

In some embodiments, contacting the compound of Formula I with human non-small cell lung cancer cells, A549, at a concentration of 100 μg/mL resulted in a growth inhibition percentage of 76 to 80%, preferably 77 to 79%, and more preferably about 78%. In some embodiments, contacting the compound of Formula I with colorectal cancer cells, HCT116, at a concentration of 100 μg/mL resulted in a growth inhibition percentage of 84 to 88%, preferably 85 to 87%, and more preferably about 86%. In some embodiments, contacting the compound of Formula I with prostate cancer cells, PC3, at a concentration of 100 μg/mL resulted in a growth inhibition percentage of 82 to 86%, preferably 83 to 85%, and more preferably about 84%. In some embodiments, contacting the compound of Formula I with pharynx squamous carcinoma cells, FaDu, at a concentration of 100 μg/mL resulted in a growth inhibition percentage of 87 to 92%, preferably 88 to 91%, and more preferably 89 to 90%. In some embodiments, contacting the compound of Formula I with triple-negative breast cancer cells, MDA-MB-468, at a concentration of 100 μg/mL resulted in a growth inhibition percentage of 89 to 94%, preferably 90 to 92, and more preferably about 90 to 91%. In some embodiments, contacting the compound of Formula I with cervical cancer cells, HeLa, at a concentration of 100 μg/mL resulted in a growth inhibition percentage of 69 to 73%, preferably 70 to 72%, and more preferably about 71%. In some embodiments, contacting the compound of Formula I with human oral epithelial normal cells, OEC, at a concentration of 100 μg/mL resulted in a growth inhibition percentage of 47 to 51%, preferably 48 to 50%, and more preferably about 49%.

The half-maximal inhibitory concentration ($IC_{50}$) value of the compound of Formula I against non-small cell lung cancer cells, A549, is 5.5 to 6.5 micrograms per milliliter (μg/mL), preferably 5.7 to 6.3 μg/mL, more preferably 5.9 to 6.1 μg/mL, and yet more preferably about 6 μg/mL. The $IC_{50}$ value of the compound of Formula I against pharynx squamous carcinoma cells, FaDu, is 4.5 to 5.5 μg/mL, preferably 4.7 to 5.3 μg/mL, more preferably 4.9 to 5.1 μg/mL, and yet more preferably about 5.03 μg/mL. The $IC_{50}$ value of the compound of Formula I against triple-negative breast cancer cells, MDA-MB-468, is 5 to 6 μg/mL, preferably 5.2 to 5.8 μg/mL, more preferably 5.4 to 5.6 μg/mL, and yet more preferably about 5.5 μg/mL. The $IC_{50}$ value of the compound of Formula I against cervical cancer cells, HeLa, is 4.5 to 5.5 μg/mL, preferably 4.7 to 5.3 μg/mL, more preferably 4.9 to 5.1 μg/mL, and yet more preferably about 5.03 μg/mL. The compound of Formula I was found to be more effective at lower concentrations in comparison to the standard drug, doxorubicin, for each of the cancers.

The compound of Formula I or an analog or derivative thereof may be used in conjunction with one or more additional compounds, in the treatment or prevention of neoplasm; of tumor or cancer cell division, growth, proliferation, and/or metastasis in a mammalian subject; induction of death or apoptosis of tumor and/or cancer cells; and/or any other form of a proliferative disorder. The compound of Formula I of the present disclosure can be formulated as a pharmaceutical composition. In some embodiments, the pharmaceutical composition, including the compound of Formula I or analog or derivative thereof, is in an amount effective for treating a patient having breast cancer, and at least one pharmaceutical additive or adjuvant.

The neoplastic activity of the tumor or cancer cells may be localized or initiated in one or more of the following: blood, brain, bladder, lung, cervix, ovary, colon, rectum, pancreas, skin, prostate gland, stomach, breast, liver, spleen, kidney, head, neck, testicle, bone (including bone marrow), thyroid gland, central nervous system, and the like. The compound of Formula I of the present disclosure or the pharmaceutical composition thereof is especially effective in the treatment or prevention of breast cancer.

A pharmaceutical composition including the compound of Formula I of the present disclosure can then be administered orally, systemically, parenterally, by inhalation spray, rectally, or topically in dosage unit formulations containing conventional non-toxic pharmaceutically acceptable carriers, adjuvants, and vehicles as desired. In some embodiments, the method of administration of the steroid or an analogue or derivative thereof is oral. In other embodiments, the compound or an analogue or derivative thereof is administered by injection, such as, for example, through a peritumoral injection.

Topical administration can also involve the use of transdermal administration, such as transdermal patches or iontophoresis devices. The term parenteral, as used herein, includes intravesical, intradermal, transdermal, subcutaneous, intramuscular, intralesional, intracranial, intrapulmonary, intracardial, intrasternal, and sublingual injections, or infusion techniques. Formulation of drugs is discussed in, for example, Hoover, John E., Remington's Pharmaceutical Sciences, Mack Publishing Co., Easton, Pa.; 1975, which is incorporated herein by reference in its entirety. Another example includes Liberman, H. A. and Lachman, L., Eds., Pharmaceutical Dosage Forms, Marcel Decker, New York, N.Y., 1980, which is incorporated herein by reference in its entirety.

Injectable preparations, for example, sterile injectable aqueous or oleaginous suspensions, can be formulated according to the known art using suitable dispersing or wetting agents and suspending agents. The sterile injectable preparation can also be a sterile injectable solution or suspension in a nontoxic, parenterally acceptable diluent or solvent, for example, as a solution in 1,3-butanediol. Among the acceptable vehicles and solvents that can be employed are water, Ringer's solution, isotonic sodium chloride solution, and the like. In addition, sterile, fixed oils are conventionally employed as a solvent or suspending medium. For this purpose, any fixed oil can be employed, including synthetic mono- or diglycerides. In addition, fatty acids such as oleic acid find use in the preparation of injectables. Dimethyl acetamide, surfactants including ionic and non-ionic detergents and polyethylene glycols can be used. Mixtures of solvents and wetting agents, such as those discussed above, are also useful. Suppositories for rectal administration of the compound or an analogue or derivative thereof can be prepared by mixing the steroid or an analogue or derivative thereof with a suitable non-irritating excipient such as cocoa butter, synthetic mono-, di-, or triglycerides, fatty acids, and polyethylene glycols that are solid at ordinary temperatures but liquid at the rectal temperature and will therefore melt in the rectum and release the drug.

Solid dosage forms for oral administration can include capsules, tablets, pills, powders, granules, and the like. In such solid dosage forms, the compounds of this disclosure are ordinarily combined with one or more adjuvants appropriate to the indicated route of administration. If administered orally, a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in a dispersion of the active compound in hydroxypropyl methylcellulose. In the case of capsules, tablets, and pills, the dosage forms can also comprise buffering agents such as sodium citrate, magnesium or calcium carbonate, or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated steroid or an analogue or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending, agents, and/or sweetening, flavoring, and perfuming agents.

The amount of compound of Formula I that can be combined with the carrier materials to produce a single dosage form varies depending upon the mammalian subject treated and the particular mode of administration.

Cancers such as, but not limited to, sarcomas, carcinomas, melanomas, myelomas, gliomas, and lymphomas can be treated or prevented with the complex provided herein. In some embodiments, a pharmaceutical composition incorporating the complex of the present disclosure is present in an amount effective for treating a patient having a proliferative disorder selected from the group consisting of head and neck cancer, breast cancer, lung cancer, colon cancer, prostate cancer, gliomas, glioblastoma, astrocytomas, glioblastoma multiforme, Bannayan-Zonana syndrome, Cowden disease, Lhermitte-Duclos disease, inflammatory breast cancer, Wilm's tumor, Ewing's sarcoma, Rhabdomyosarcoma, ependymoma, medulloblastoma, kidney cancer, liver cancer, melanoma, pancreatic cancer, sarcoma, osteosarcoma, giant cell tumor of bone, thyroid cancer, lymphoblastic T cell leukemia, Chronic myelogenous leukemia, Chronic lymphocytic leukemia, Hairy-cell leukemia, acute lymphoblastic leukemia, acute myelogenous leukemia, AML, Chronic neutrophilic leukemia, Acute lymphoblastic T cell leukemia, plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, Hodgkin's lymphoma, non-Hodgkin's lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), testicular cancer, and the like. In some embodiments, the pharmaceutical composition including the compound of Formula I is especially effective in the treatment or prevention of breast cancer, particularly triple-negative breast cancer.

The methods for treating cancer and other proliferative disorders described herein inhibit, remove, eradicate, reduce, regress, diminish, arrest, or stabilize a cancerous tumor, including at least one of the tumor growth, tumor cell viability, tumor cell division, and proliferation, tumor metabolism, blood flow to the tumor, and metastasis of the tumor. In some embodiments, after treatment with the compound of Formula I or a pharmaceutical composition thereof, the size of a tumor, whether by volume, weight, or diameter, is reduced by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, after treatment with the compound of Formula I or a pharmaceutical composition thereof, the size of a tumor does not reduce but is maintained the same as the tumor size before treatment. Methods of assessing tumor size include, but are not limited to, CT scan, MRI, DCE-MRI, and PET Scan.

In some embodiments, the method for treating cancer and other proliferative disorders involves the administration of a unit dosage or a therapeutically effective amount of the compound of Formula I or a pharmaceutical composition thereof to a mammalian subject (preferably a human subject) or a patient in need thereof. As used herein, "a subject in need thereof" refers to a mammalian subject, preferably a human subject, who has been diagnosed with, is suspected of having, is susceptible to, is genetically predisposed to, or is at risk of having at least one form of cancer. During administration, the compound of Formula I is contacted with breast cancer in the form of at least one of a monolayer of cells, a multicellular tumor spheroid (MCTS), and an in vivo xenograft tumor. On administration, the complex induces apoptosis through one of the may pathways—p53, BAX, caspases, BCL-2, MMP2, and MMP9.

The dosage and treatment duration are dependent on factors such as the bioavailability of a drug, administration mode, toxicity of a drug, gender, age, lifestyle, body weight, the use of other drugs and dietary supplements, cancer stage, tolerance, and resistance of the body to the administered drug, and the like, then determined and adjusted accordingly. The compound of Formula I or a pharmaceutical composition thereof may be administered in a single dose or multiple individual divided doses. In some embodiments, the interval of time between the administration of complex or a pharmaceutical composition thereof and the administration of one or more additional therapies may be about 1-5 minutes, 1-30 minutes, 30-60 minutes, 90 minutes, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, 5 years, 10 years, indefinitely, or any period in between. In certain embodiments, the compound and one or more additional therapies are administered less than 1 day, 1 week, 2 weeks, 3 weeks, 4 weeks, one month, 2 months, 3 months, 6 months, 1 year, 2 years, or 5 years apart.

In certain embodiments, the compound of Formula I of the present disclosure or a pharmaceutical composition thereof may be used in combination with one or more other antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosamide, irinotecan, lomustine, mechclorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguaniue), and tipifarnib. Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin, and enzastaurin. Examples for antineoplastic agents which are antibodies comprise trastuzumab, cetuximab, panitumumab, rituximab, bevacizumab, mapatumumab, conatumumab, lexatumumab, and the like.

EXAMPLES

The disclosure will now be illustrated with working examples, which are intended to illustrate the working of the disclosure and not intended to restrictively imply any limitations on the scope of the present disclosure, as many variations thereof are possible without departing from the spirit and scope of the present disclosure. The working examples depict an example of the method of the present disclosure. The following examples demonstrate a method of cytotoxically treating cancer cells by contacting the cancer cells with a composition comprising a compound of Formula I, and a process of preparing the compound of Formula I. The examples are provided solely for illustration and are not to be construed as limitations of the present disclosure.

Example 1: Synthesis of 3-(2-(1,3-dioxoisoindolin-2-yl)ethyl)-5-(2-hydroxy-5-nitrobenzylidene)thiazolidine-2,4-dione (Formula I)

Figure 2:
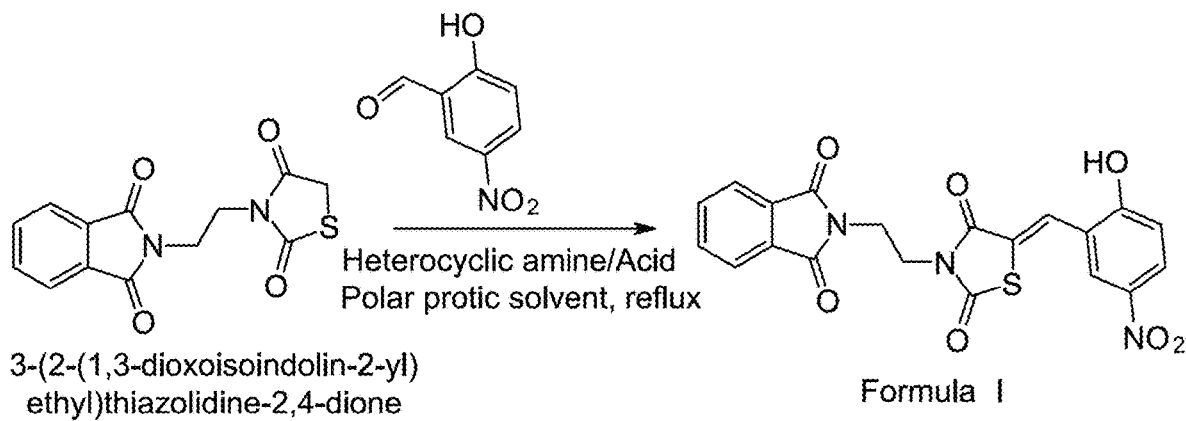
FIG. 2 is a reaction scheme depicting a process of forming the compound of Formula I, according to certain embodiments.

3-(2-(1,3-Dioxoisoindolin-2-yl)ethyl)-5-(2-hydroxy-5-nitrobenzylidene)thiazolidine-2,4-dione (Formula I) was synthesized from the reaction of 3-(2-(1,3-dioxoisoindolin-2-yl)ethyl)thiazolidine-2,4-dione with 2-hydroxy-5-nitrobenzaldehyde in the presence of catalytic amounts of acetic acid and piperidine. A reaction scheme for the synthesis of the compound of Formula I is provided in FIG. 2. In brief, 3-(2-(1,3-dioxoisoindolin-2-yl)ethyl)thiazolidine-2,4-dione (1 mmol) and 2-hydroxy-5-nitrobenzaldehyde (1.1 mmol) were dissolved in ethanol. To this mixture, 50 µL acetic acid and 50 µL piperidine were added and the mixture was refluxed for 8 hours. The pale-yellow precipitate formed was filtered while hot to give the compound of Formula I in 85% yield (melting point=255-256° C.).

$^1$H NMR (400 MHZ, DMSO-d6) δ 12.24 (s, 1H, OH), 8.15 (s, 1H, CH=), 7.91 (s, 1H, Ar—H), 7.82 (tdd, J=9.9, 6.6, 3.5 Hz, 5H, Ar—H), 7.05-6.99 (m, 1H, Ar—H), 3.93-3.86 (m, 2H, CH2), 3.86-3.82 (m, 2H, CH2); 13C NMR (101 MHZ, DMSO-d6) δ 168.26, 168.18, 167.72, 165.98, 160.14, 140.05, 135.07, 131.81, 128.28, 127.10, 125.30, 123.67, 120.67, 117.35, 39.50, 35.93; high-resolution mass spectrometry (HRMS) calculated for $C_{20}H_{13}N_3O_7S$ [M+]: 439.05467, found 440.05470 [M++1], 441.05806 [M++2], 442.05050 [M++3].

Figure 3:
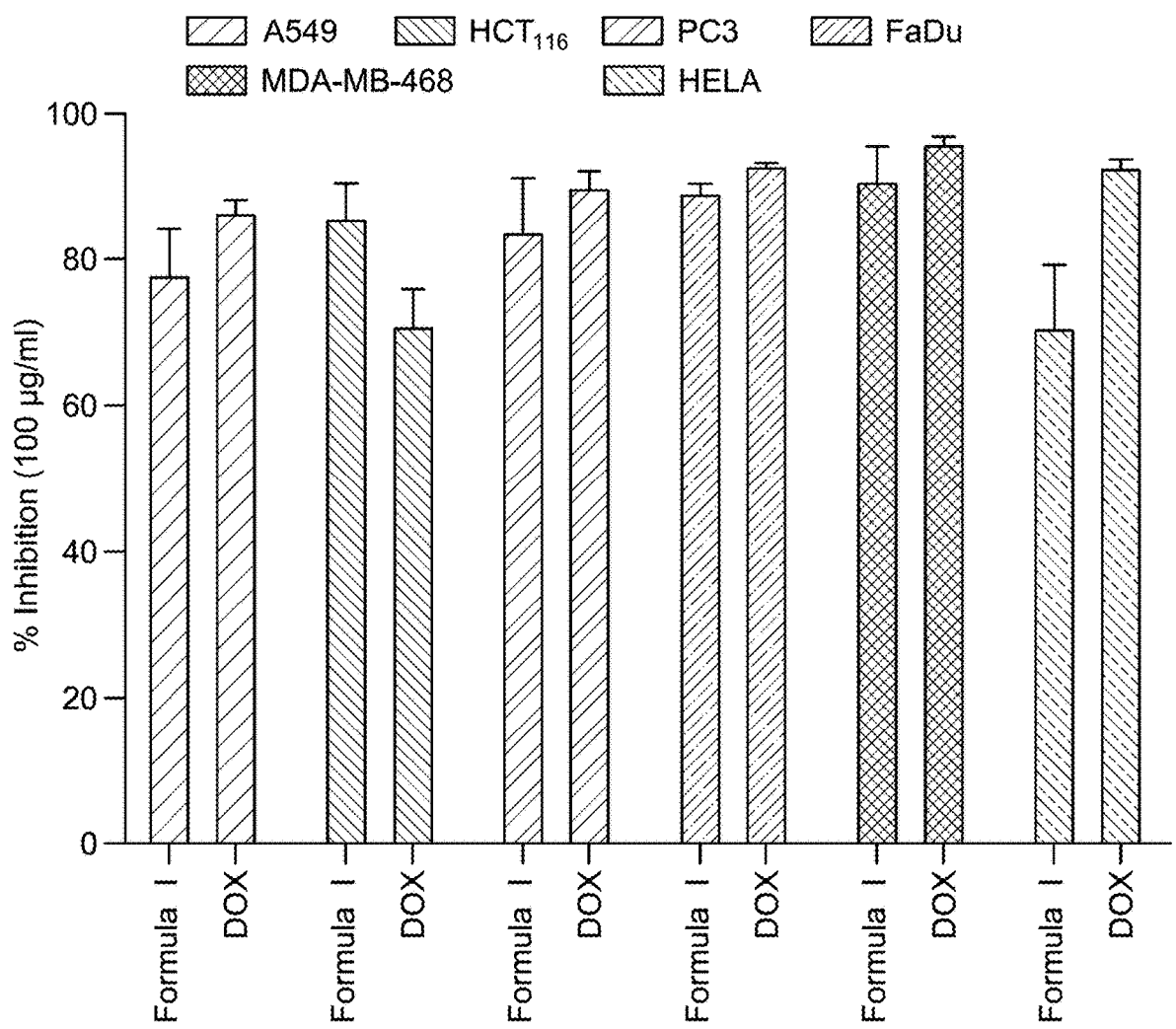
FIG. 3 is a comparative bar graph depicting growth inhibition in various cancer cell lines, with the compound of Formula I and a reference drug, doxorubicin, according to certain embodiments.

Example 2: Growth Inhibition of Cancerous Cells 3-(2-(1,3-Dioxoisoindolin-2-yl)ethyl)-5-(2-hydroxy-5-nitrobenzylidene)thiazolidine-2,4-dione (Formula I) showed very strong antitumor activities against human non-small cell lung cancer (A549), colorectal carcinoma (HCT116), prostate cancer (PC3), pharynx squamous carcinoma (FaDu), triple-negative breast cancer (MDA-MB-468), and cervical cancer (HeLa) with growth inhibition percentages of 77.95%, 85.73%, 83.84%, 89.10%, 90.83%, and 70.76% at a concentration of 100 μg/mL, as shown in FIG. 3. These results were compared to doxorubicin in A549, HCT116, PC3, FaDu, MDA-MB-468, and HeLa, with growth inhibition percentages of 86.43%, 71.00%, 89.94%, 92.93%, 96.02%, and 92.70%, respectively. Moreover, Formula I recorded a low growth inhibition percentage of 48.89% towards the human oral epithelial normal cell line (OEC), compared to 57.89% for doxorubicin.

The $IC_{50}$ values towards the cancer cell lines A549, FaDu, MDA-MB-468, and HeLa were recorded to be 6.00 g/mL, 5.03 μg/mL, 5.50 μg/mL, and 5.03 μg/mL, respectively. These values were compared to doxorubicin as a reference drug, which showed $IC_{50}$ values of 7.63 μg/mL, 13.16 μg/mL, 7.76 μg/mL, and 4.83 μg/mL against A549, FaDu, MDA-MB-468, and HeLa cancer cell lines, respectively.

A potent compound, a compound of Formula I, showed antitumor activities against human non-small cell lung cancer (A549), colorectal carcinoma (HCT116), prostate cancer (PC3), pharynx squamous carcinoma (FaDu), triple-negative breast cancer (MDA-MB-468), and cervical cancer (HeLa) at a concentration of 100 μg/mL, compared to doxorubicin.

Numerous modifications and variations of the present disclosure are possible in light of the above teachings. It is therefore to be understood that within the scope of the appended claims, the disclosure may be practiced otherwise than as specifically described herein.

The invention claimed is:

1. A method of cytotoxically treating cancer cells, comprising:
    contacting the cancer cells with a composition comprising a compound of Formula I in combination with one or more other antineoplastic or chemotherapeutic agents:

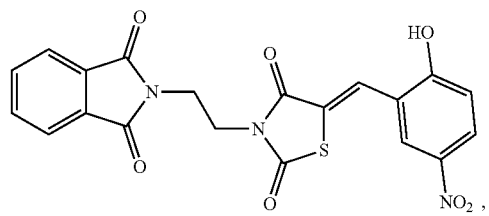

wherein the compound of Formula I is contacted with the cancer cells in an amount effective to reduce the number of cancer cells by at least 50%,
    wherein the contacting includes administering the composition orally, systemically or parenterally with a carrier or excipient.

2. The method of claim 1, wherein the contacting includes inhibiting cell growth of the cancer cells through apoptosis.

3. The method of claim 2, wherein the apoptosis occurs through at least one of a p53 pathway, a BAX pathway, a caspases pathway, a BCL-2 pathway, an MMP2 pathway, and an MMP9 pathway.

4. The method of claim 1, further comprising:
    making the compound of Formula I by:
    dissolving 3-(2-(1,3-dioxoisoindolin-2-yl)ethyl)thiazolidine-2,4-dione and 2-hydroxy-5-nitrobenzaldehyde in a polar protic solvent to form a reaction mixture;
    adding an acid and a heterocyclic amine to the reaction mixture; and
    refluxing the reaction for 6 to 10 hours to form the compound of Formula I.

5. The method of claim 4, wherein a molar ratio of 3-(2-(1,3-dioxoisoindolin-2-yl)ethyl)thiazolidine-2,4-dione to 2-hydroxy-5-nitrobenzaldehyde is from 1:0.8 to 1:1.5.

6. The method of claim 4, wherein the compound of Formula I is formed in a yield of 83 to 87% based on an initial amount of the 3-(2-(1,3-dioxoisoindolin-2-yl)ethyl)thiazolidine-2,4-dione.

7. The method of claim 1, wherein the contacting includes contacting the compound of Formula I with human non-small cell lung cancer cells, A549, at a concentration of 100 μg/mL to provide a growth inhibition percentage of 76 to 80%.

8. The method of claim 1, wherein the contacting includes contacting the compound of Formula I with colorectal carcinoma cell line, HCT116, at a concentration of 100 μg/mL to provide a growth inhibition percentage of 84 to 88%.

9. The method of claim 1, wherein the contacting includes contacting the compound of Formula I with prostate cancer cells, PC3, at a concentration of 100 μg/mL to provide a growth inhibition percentage of 82 to 86%.

10. The method of claim 1, wherein the contacting includes contacting the compound of Formula I with pharynx squamous carcinoma cells, FaDu, at a concentration of 100 μg/mL to provide a growth inhibition percentage of 87 to 92%.

11. The method of claim 1, wherein the contacting includes contacting the compound of Formula I with triple-negative breast cancer cells, MDA-MB-468, at a concentration of 100 μg/mL to provide a growth inhibition percentage of 89 to 94%.

12. The method of claim 1, wherein the contacting includes contacting the compound of Formula I with cervical cancer cells, HeLa, at a concentration of 100 μg/mL to provide a growth inhibition percentage of 69 to 73%.

13. The method of claim 1, wherein the contacting includes contacting the compound of Formula I with human non-small cell lung cancer cells, A549, to provide a half-maximal inhibitory concentration ($IC_{50}$) value of 5.5 to 6.5 μg/mL.

14. The method of claim 1, wherein the contacting includes contacting the compound of Formula I with pharynx squamous carcinoma cells, FaDu, to provide a half-maximal inhibitory concentration ($IC_{50}$) value of 4.5 to 5.5 μg/mL.

15. The method of claim 1, wherein the contacting includes contacting the compound of Formula I with triple-negative breast cancer cells, MDA-MB-468, to provide a half-maximal inhibitory concentration ($IC_{50}$) value of 5 to 6 μg/mL.

16. The method of claim 1, wherein the contacting includes contacting the compound of Formula I with cervical cancer cells, HeLa, to provide a half-maximal inhibitory concentration ($IC_{50}$) value of 4.5 to 5.5 μg/mL.

17. The method of claim 1, wherein the contacting includes contacting the compound of Formula I with human oral epithelial normal cells, OEC, at a concentration of 100 μg/mL to provide a growth inhibition percentage of 47 to 51%.

18. The method of claim 1, wherein the composition further comprises one or more pharmaceutically acceptable carriers.

19. The method of claim 18, wherein the composition is in the form of a pill, a liquid, a shot, a cream, and a patch.

20. The method of claim 1, wherein the compound of Formula I has a melting point of 252 to 259° C.

\* \* \* \* \*